United States Patent
Joo et al.

(10) Patent No.: US 10,595,721 B2
(45) Date of Patent: Mar. 24, 2020

(54) SURGICAL APPARATUS FOR LAMELLAR KERATOPLASTY COMPRISING AN OCT DETECTION UNIT

(71) Applicant: The Catholic University of Korea Industry-Academic Cooperation Foundation, Seoul (KR)

(72) Inventors: Choun Ki Joo, Seoul (KR); Young Sik Yoo, Seoul (KR); Suc Bei Moon, Seoul (KR)

(73) Assignee: The Catholic University of Korea Industry-Academic Cooperation Foundation, Seoul (KR)

( * ) Notice: Subject to any disclaimer, the term of this patent is extended or adjusted under 35 U.S.C. 154(b) by 316 days.

(21) Appl. No.: 15/572,686

(22) PCT Filed: Jun. 7, 2017

(86) PCT No.: PCT/KR2017/005903
§ 371 (c)(1),
(2) Date: Nov. 8, 2017

(87) PCT Pub. No.: WO2017/213412
PCT Pub. Date: Dec. 14, 2017

(65) Prior Publication Data
US 2018/0220884 A1    Aug. 9, 2018

(30) Foreign Application Priority Data
Jun. 8, 2016 (KR) ................. 10-2016-0071203

(51) Int. Cl.
*A61B 3/10* (2006.01)
*A61F 9/008* (2006.01)
(Continued)

(52) U.S. Cl.
CPC ............ *A61B 3/102* (2013.01); *A61B 5/0066* (2013.01); *A61F 9/008* (2013.01); *A61F 9/0008* (2013.01);
(Continued)

(58) Field of Classification Search
CPC .. A61F 9/007; A61F 9/00736; A61F 9/00781; A61F 9/00008; A61F 9/0017;
(Continued)

(56) References Cited

U.S. PATENT DOCUMENTS 9,539,143 B2 * 1/2017 Holliday ............. A61F 9/00838
9,552,660 B2 * 1/2017 Tripathi ................. G06T 19/00
(Continued)

FOREIGN PATENT DOCUMENTS

CN          102098993 A       6/2011
KR     10-2009-0012995 A      9/2009
(Continued)

OTHER PUBLICATIONS

International Search Report and Written Opinion for International Application No. PCT/KR2017/005903, entitled: "Surgical Device for Lamella Corneal Transplant Surgery Comprising OCT Detecting Portion," dated Dec. 14, 2017.

(Continued)

*Primary Examiner* — Dianne Dornbusch
(74) *Attorney, Agent, or Firm* — Hamilton, Brook, Smith & Reynolds, P.C.

(57) ABSTRACT

The present invention relates to a surgical apparatus for dissecting a part of cornea during lamellar keratoplasty, which provides a surgical apparatus comprising: an injector unit including a hollow injection needle having a bevel structure at one end; a laser unit for emitting a laser for OCT imaging; an OCT detection unit for photographing a tomographic image of the cornea using the laser; a laser light (Continued)

sensor located on an inner surface of the bevel structure of the injection needle and connected to the laser unit and the OCT detection unit through an optical fiber; and a depth adjusting unit for adjusting a depth of the injection needle in the cornea according to an operation of a user.

18 Claims, 4 Drawing Sheets

(51) Int. Cl.
    *A61F 9/00*     (2006.01)
    *A61B 5/00*     (2006.01)

(52) U.S. Cl.
    CPC ............... *A61F 2009/00851* (2013.01); *A61F 2009/00872* (2013.01)

(58) Field of Classification Search
    CPC .. A61F 2009/00872; A61F 2009/00853; A61F 2009/00882; A61F 2009/00881; A61B 3/10; A61B 3/102
    See application file for complete search history.

(56) References Cited

U.S. PATENT DOCUMENTS

| | | | | |
|---|---|---|---|---|
| 2008/0255578 | A1* | 10/2008 | Neusidl | A61F 9/0017 606/107 |
| 2008/0281341 | A1* | 11/2008 | Miller | A61F 2/14 606/166 |
| 2009/0270982 | A1* | 10/2009 | Torres | A61F 2/148 623/5.11 |
| 2010/0036488 | A1* | 2/2010 | de Juan, Jr. | A61F 2/14 623/5.16 |
| 2012/0095439 | A1* | 4/2012 | de Juan, Jr. | A61F 9/0017 604/506 |
| 2012/0116234 | A1* | 5/2012 | Farcy | A61B 5/0071 600/478 |
| 2013/0011332 | A1* | 1/2013 | Boyden | A61M 37/0015 424/1.11 |
| 2013/0324942 | A1* | 12/2013 | de Juan, Jr. | A61K 9/0051 604/246 |
| 2014/0358125 | A1* | 12/2014 | de Juan, Jr. | A61K 9/0051 604/521 |
| 2016/0151202 | A1* | 6/2016 | Scarcelli | A61F 9/008 606/5 |
| 2016/0302659 | A1* | 10/2016 | Boss | A61B 3/102 |
| 2017/0100282 | A1* | 4/2017 | Seiler | A61F 9/00827 |
| 2017/0189228 | A1* | 7/2017 | Yang | A61B 3/113 |

FOREIGN PATENT DOCUMENTS

| | | |
|---|---|---|
| KR | 10-2013-0038902 A | 4/2013 |
| KR | 2014-0104584 A | 8/2014 |
| KR | 10-2014-0110206 A | 9/2014 |
| KR | 10-2014-0104585 A | 10/2014 |
| WO | 2017/213412 A1 | 12/2017 |

OTHER PUBLICATIONS

International Search Report for International Application No. PCT/KR2017/005903, (English Translation) entitled: "Surgical Device for Lamella Corneal Transplant Surgery Comprising OCT Detecting Portion," dated Dec. 14, 2017.

\* cited by examiner

SURGICAL APPARATUS FOR LAMELLAR KERATOPLASTY COMPRISING AN OCT DETECTION UNIT

RELATED APPLICATIONS

This Application is the U.S. National Stage of International Application No. PCT/KR2017/005903, filed Jun. 7, 2017, which designates the U.S., published in Korean, and claims priority under 35 U.S.C. §§ 119 or 365(c) to Korean Application No. 10-2016-0071203, filed Jun. 8, 2016. The entire teachings of the above applications are incorporated herein by reference.

TECHNICAL FIELD

The present invention relates to a surgical apparatus for lamellar keratoplasty comprising an OCT detection unit.

BACKGROUND ART

Lamellar keratoplasty (Deep anterior lamellar keratoplasty, Descemet stripping endothelial keratoplasty, Descemet membrane endothelial keratoplasty) is a procedure that only replaces abnormal layers in the recipient cornea, which is a transplantation method that increases the success rate of transplantation and lowers post-transplant complications compared to the conventional penetrating keratoplasty method of transplanting the whole cornea. Due to its superiority over the penetrating keratoplasty, lamellar keratoplasty is already commonly practiced in the US and Europe, and its frequency of practice is higher than that of penetrating keratoplasty.

However, lamellar keratoplasty requires a process of reshaping the corneas of both the graft recipient and the donor, and it is now performed manually depending on the operator's senses. Hence, there is a problem that the accuracy and reproducibility of the corneal dissection vary widely depending on the operator's experience and dexterity.

Optical coherence tomography (OCT), which uses a light interference technique to acquire a tomographic image, can be used to acquire a corneal tomographic image before surgery and identify the interfaces between corneal layers in advance. Such OCT technology is similarly disclosed in Korean Patent Laid-Open Publication No. 10-2014-0104584.

However, even if there is a tomographic image available through OCT, the operation of manual dissection of the cornea may still depend on the operator's dexterity, and the depth of the injection needle depends on the operator's experience. There still is a problem that the accuracy and reproducibility of the corneal reshaping vary widely.

Therefore, in order to increase the success rate of the lamellar keratoplasty and to effectively use a limited number of donor corneas, there is a high need for a technique capable of accurately reshaping the cornea with less variation in reproducibility.

DISCLOSURE

Technical Problem

It is an object of the present invention to solve the above-described problems of the prior art and the technical problems experienced from the past.

The inventors of the present application have conducted intensive research and various experiments. As a result, the present invention provides a surgical apparatus for separating a portion of a cornea during a partial keratoplasty, which is located on the inner side of a bevel structure of an injection needle, a laser light sensor connected to the laser unit and the OCT detection unit through an optical fiber, and a depth adjusting unit for adjusting the depth of the injection needle in the cornea according to a manipulation of a user. Due to the constitution above, the cornea can be formed accurately without degrading reproducibility, and success rate of the corneal transplantation can be markedly improved. The present invention has been accomplished on the basis of this finding.

Technical Solution

Accordingly, a surgical apparatus for partial dissection of cornea during lamellar keratoplasty comprises: an injector unit including a hollow injection needle having a bevel structure at one end; a laser unit for emitting a laser for OCT imaging; an OCT detection unit for photographing a tomographic image of the cornea using the laser; a laser light sensor located on an inner surface of the bevel structure of the injection needle and connected to the laser unit and the OCT detection unit through an optical fiber; and a depth adjusting unit for adjusting a depth of the injection needle in the cornea according to an operation of a user.

In one specific example, the injector unit may include: a cylinder; a piston having an outer diameter corresponding to an inner diameter of the cylinder; a coupling tube communicating with the cylinder positioned at one end of the cylinder, and having a narrowing outer diameter; and a fixing tube communicating with the coupling tube and having an inner diameter corresponding to the outer diameter of the coupling tube, the fixing tube being connected to the coupling tube in a fitting manner and fixing the injection needle on the opposite side of the coupling tube In one specific example, it may have a structure where the optical fiber connected to the laser light sensor is located in the injection needle, and the optical fiber is connected to the laser unit and the OCT detection unit by extending outward through a portion where the coupling tube and the fixing tube is connected in a fitting manner.

In one specific example, the piston may have a structure that compresses air in the cylinder either manually or electrically so that the air is discharged through the injection needle when the injection needle reaches a set depth in the cornea.

In one specific example, the laser light sensor may have a slope structure in which one end of the laser light sensor has an angle of 30 to 60 degrees such that the laser light can be injected toward an open direction of the bevel structure of the injection needle, and a reflection portion for reflecting the laser may be formed in the slope structure of the laser light sensor.

In one specific example, the reflection portion may have a structure in which a metal is coated or a mirror is attached on an outer surface of the slope structure.

In one specific example, the laser unit may include a laser engine and a laser scanner.

In one specific example, the OCT detection unit may include an OCT scanner and an image processing unit, and the image processing unit may visualize a tomographic structure of at least two layers selected from the group consisting of the corneal epithelium, Bowman's membrane, corneal stroma, Descemet's membrane, and corneal endothelium based on an electrical signal of the OCT scanner.

In one specific example, the depth adjusting unit may include an electric motor for adjusting the position of the cylinder while being in contact with the outer surface of the cylinder of the injector unit to adjust the depth of the injection needle.

In one specific example, the electric motor may adjust the depth of the injection needle at a speed of 100 μm/sec to 500 μm/sec.

In one specific example, the depth adjusting unit may further include a speed control unit for adjusting the insertion speed of the injection needle according to an operation of a user.

In one specific example, the speed control unit may be a pressure sensing pedal that increases the insertion speed of the injection needle as the applied pressure increases.

In one specific example, the surgical apparatus may further comprise a control unit for controlling the laser unit, the OCT detection unit, and the depth adjusting unit.

In one specific example, the control unit may control the depth adjusting unit to prevent the injection needle from being inserted over the set depth.

In one specific example, the surgical apparatus may further comprise an alarm device controlled via the control unit, and the control unit may control the alarm device so that the alarm sounds when the injection needle reaches the set depth.

In one specific example, the set depth may be a depth of one of the anatomical interfaces between of the corneal epithelium, the Bowman's membrane, the corneal stroma, the Descemet's membrane, and the corneal endothelial.

BEST MODE

Hereinafter, embodiments of the present invention will be described with reference to the accompanying drawings. However, it is for a better understanding of the present invention, and the scope of the present invention is not limited thereto.

Figure 1:
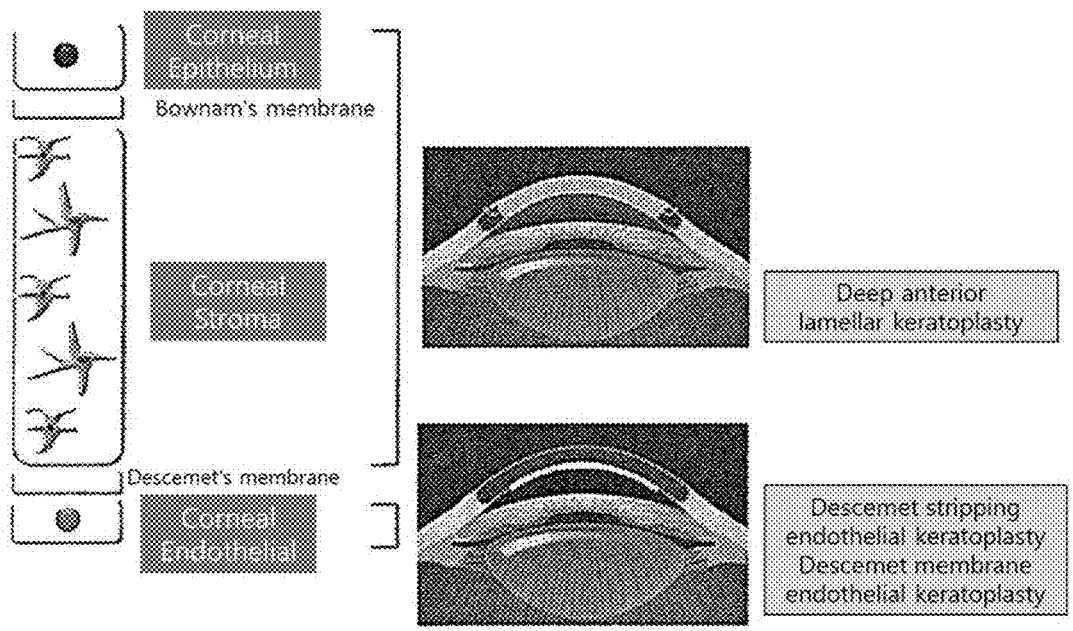
FIG. 1 schematically shows the structure of the cornea and the types of the lamellar keratoplasty.

FIG. 1 schematically shows the structure of the cornea and the types of the lamellar keratoplasty.

Referring to FIG. 1, the cornea is composed of five layers: from the outer side of the cornea, the corneal epithelium, the Bowman's membrane, the corneal stroma, the Descemet's membrane, and the corneal endothelial.

Lamellar keratoplasty is a method of transplanting only some of the five layers of the cornea rather than transplanting all parts of the cornea from the corneal epithelium to the corneal endothelial.

Particularly, depending on the portion of the cornea to be implanted, it is classified further as deep anterior lamellar keratoplasty, Descemet stripping endothelial keratoplasty, and Descemet membrane endothelial keratoplasty, etc.

Figure 2:
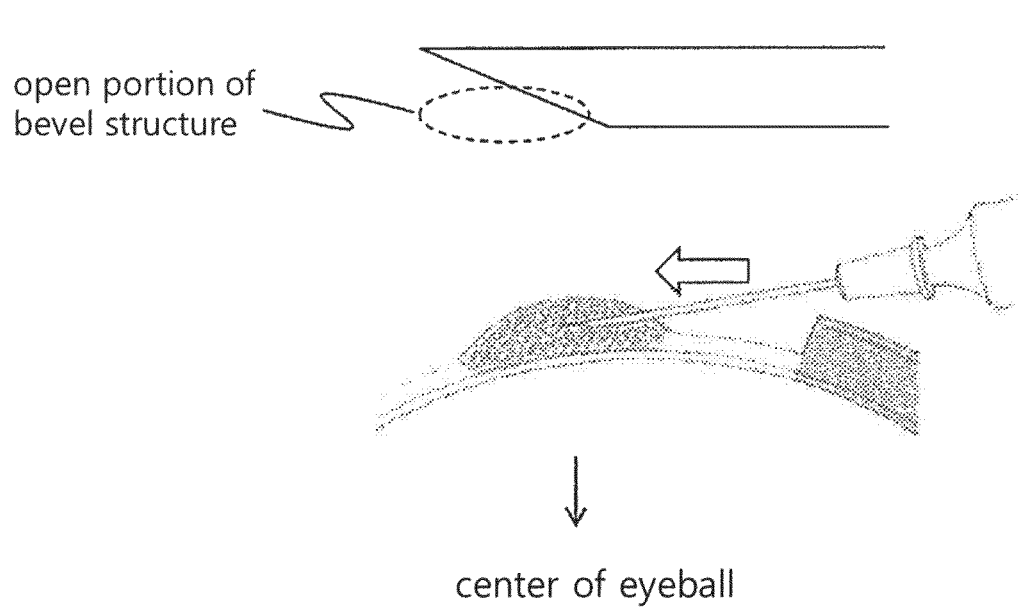
FIGS. 2 and 3 are a schematic diagram and a photograph illustrating a big bubble technique for separating a portion of the cornea in the lamellar keratoplasty, respectively.
Figure 3:
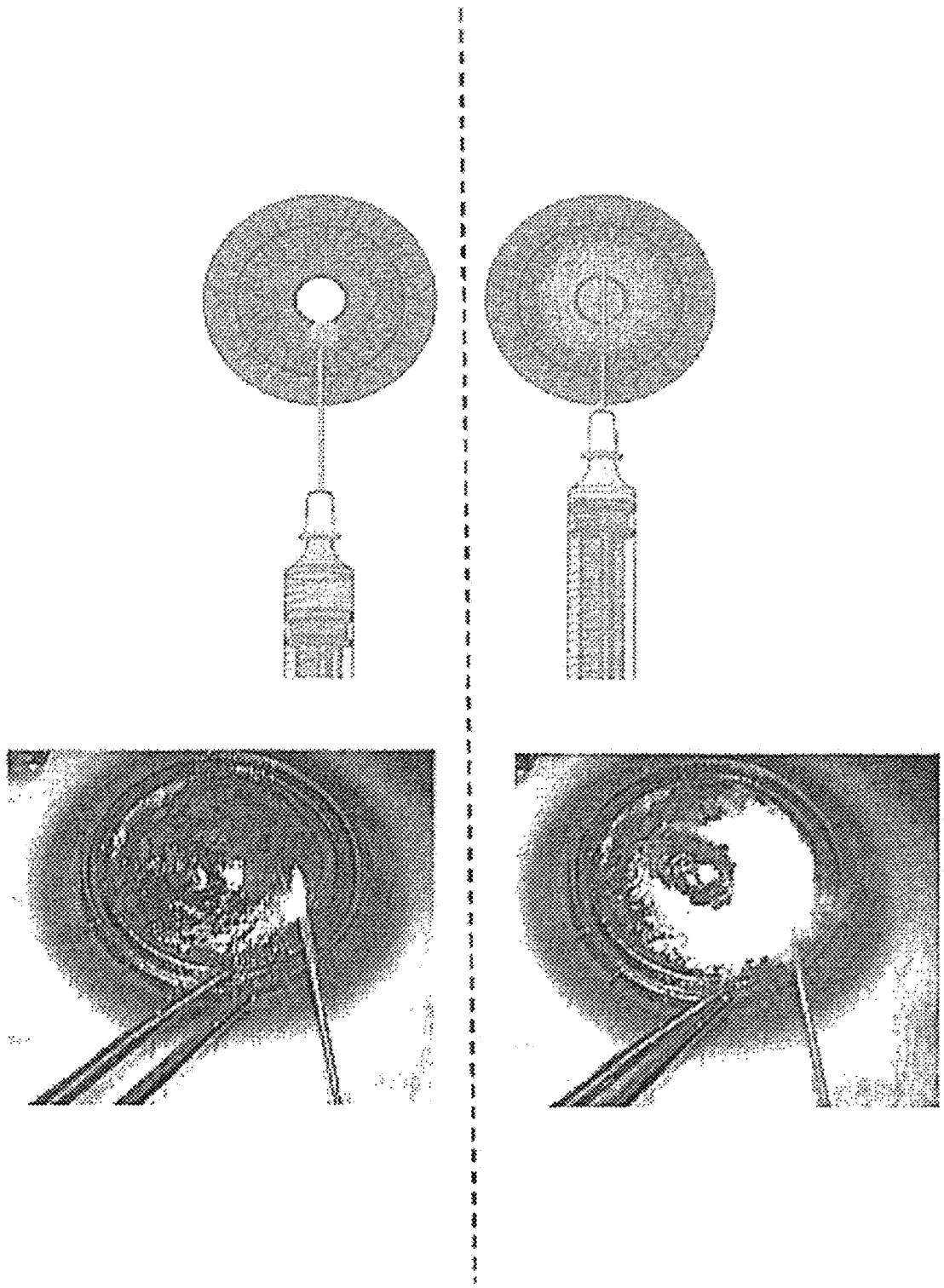

FIGS. 2 and 3 illustrate a big bubble technique for separating a portion of the cornea in lamellar keratoplasty.

Referring to FIG. 2, in order to separate a portion of the cornea using the big bubble technique, the injection needle is inserted in the lateral direction of the cornea rather than the direction perpendicular to the center of the eye.

When using the big bubble technique, the injection needle needs to be inserted so that the open portion of the bevel structure of the injection needle faces the center of the eyeball to let air be injected into the anatomical interface of the cornea layers. When the open portion of the bevel structure of the injection needle is inserted upward, air is injected upward and it is difficult to accurately inject air into the anatomical interface of the cornea layer.

For reference, it is common that the cornea is incised circularly in a plane before insertion of the injection needle, so that a portion of the cornea is more easily separated after performing the big bubble technique.

Referring to FIG. 3, when a desired depth is reached in the cornea while inserting the injection needle in the lateral direction of the cornea, bubbles are formed through injection of air to separate the cornea layers by forming bubbles at the anatomical interface of the cornea layers. The left side of FIG. 3 shows the state before the air injection, and the right side of FIG. 3 shows the state after the air injection.

The thickness of the cornea is about 520 μm to 530 μm with some individual deviation, and it should be adjusted in the order of micrometers by adjusting the depth of insertion of the injection needle during lamellar keratoplasty. The technique of inserting the injection needle sensitively is very difficult even for a highly skilled operator, and it is very difficult to reshape the cornea to a desired thickness.

Figure 4:
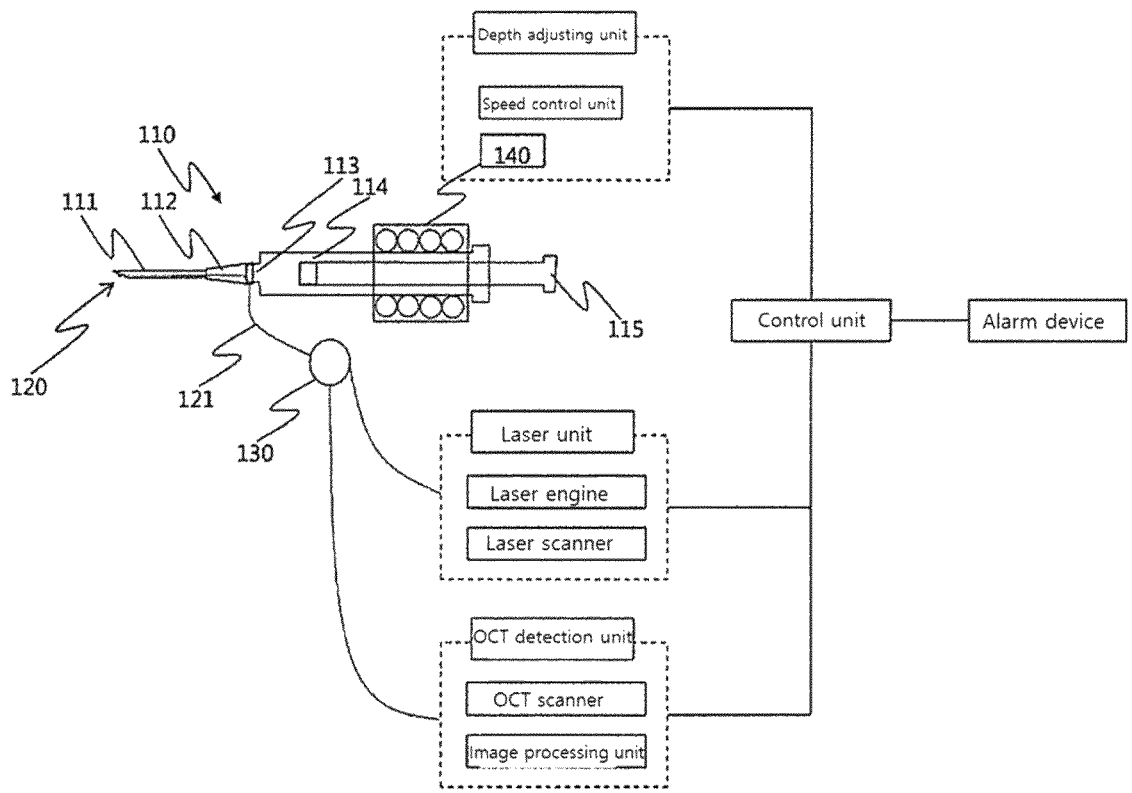
FIG. 4 is a schematic diagram showing a surgical apparatus for the lamellar keratoplasty according to one embodiment of the present invention.
Figure 5:
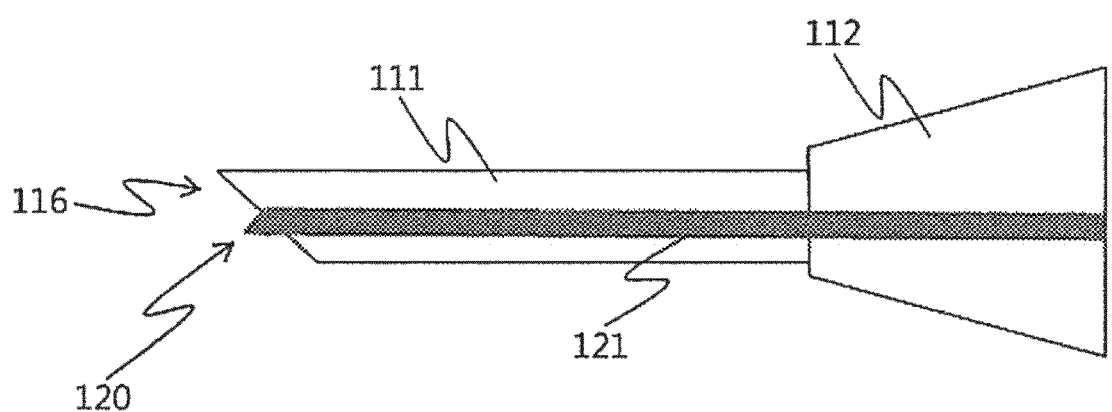
FIG. 5 is an enlarged view of the injection needle of the injector unit and laser light sensor of FIG. 4.
Figure 6:
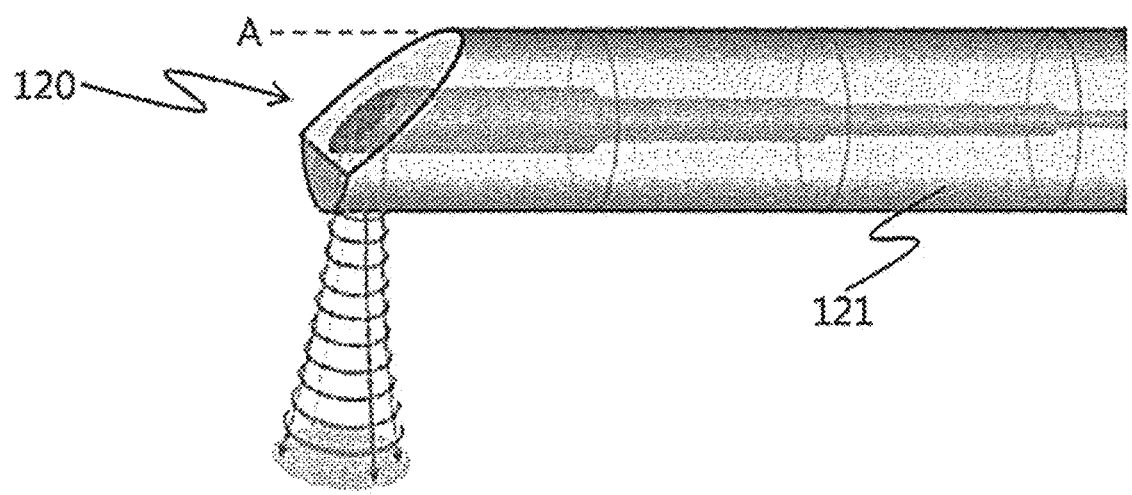
FIG. 6 is an enlarged view of the laser light sensor and the optical fiber of FIG. 5.

FIG. 4 shows a surgical apparatus for lamellar keratoplasty according to one embodiment of the present invention. FIG. 5 is an enlarged view of the injection needle of the injector unit and laser light sensor of FIG. 4. FIG. 6 is an enlarged view of the laser light sensor and the optical fiber of FIG. 5.

Referring to FIG. 4, a surgical apparatus 100 according to the present invention includes an injector unit 110, a laser unit, an OCT detection unit, a laser light sensor 120, and a depth adjusting unit. Specifically, the injector unit 110 has a cylinder 114, a piston 115 having an outer diameter corresponding to an inner diameter of the cylinder, a coupling tube 113, a fixing tube 112 having an inner diameter corresponding to an outer diameter of the coupling tube 113, and a hollow injection needle 111 fixed to the fixing tube.

The coupling tube 113 is located at one end of the cylinder 114 and communicates with the cylinder 114 and its outer diameter becomes narrower.

The fixing tube 112 is connected to the coupling tube 113 in a fitting manner and has an inner diameter corresponding to the outer diameter of the coupling tube 113. The fixing tube 112 has the injection needle 111 fixed on an opposite side of the coupling tube 113.

The injection needle 111 has a hollow structure, and its opposite end of the fixing tube 112 to the coupling tube 113 has a bevel structure.

The piston 115 has a structure that manually compresses the air in the cylinder 114 so that air is discharged through the injection needle 111 when the injection needle 111 reaches a set depth in the cornea. However, the present invention is not limited to this, and in the case where the piston 115 operates by an electric motor is also included in the present invention.

The laser light sensor 120 is located on the inner side of the bevel structure of the injection needle 111 and is connected to the laser unit and the OCT detection unit through the optical fiber 121. In particular, a coupler 130 is connected to the center of the optical fiber 121 so that the optical fiber is branched and connected to both the laser unit and the OCT detection unit.

When the laser light sensor 120 is positioned on the inner side of the bevel structure of the injection needle 111, the position of the sensor may approach closer to the anatomical interface of the cornea layers while the injection needle 111 is inserted into the cornea. Thus, the laser light sensor 120 can more accurately measure the anatomical interface of the cornea layers.

In addition, the volume occupied by the optical fiber 121 inside the injection needle 111 is 20% to 80% of the total volume of the inside of the injection needle 111 which has a hollow structure. The remaining 20% to 80% forms an air passage for injecting air.

Referring to FIGS. 5 and 6 with FIG. 4, an optical fiber 121 connected to the laser light sensor 120 is positioned inside the injection needle 111, the optical fiber 121 is connected to the laser unit and the OCT detection unit by the coupler 130 by extending outward through a portion where the coupling tube 113 and the fixing tube 112 are connected in a fitting manner. However, this is merely an example, and the optical fiber may be connected outward by perforating a portion of the injection needle 111 or the fixing tube 112 and sealing the perforated site.

The laser light sensor 120 has a sloped structure in which a left end of the laser light sensor 120 has an angle of 30 to 60 degrees to the horizontal direction (Dashed line A), which is a traveling direction of the optical fiber 120, such that the laser light can be injected downward which is an opened direction of the bevel structure 116 of the injection needle 111. In the slope structure of the laser light sensor 120, a reflection portion is formed to reflect the laser so that the traveling direction of the laser can be directed downward where the center of the eye is located.

The reflection portion is not particularly limited as long as it can change the direction by reflecting the laser, but it may have a structure in which metal is coated or a mirror is attached on an outer surface of a slope structure.

Figure 7:
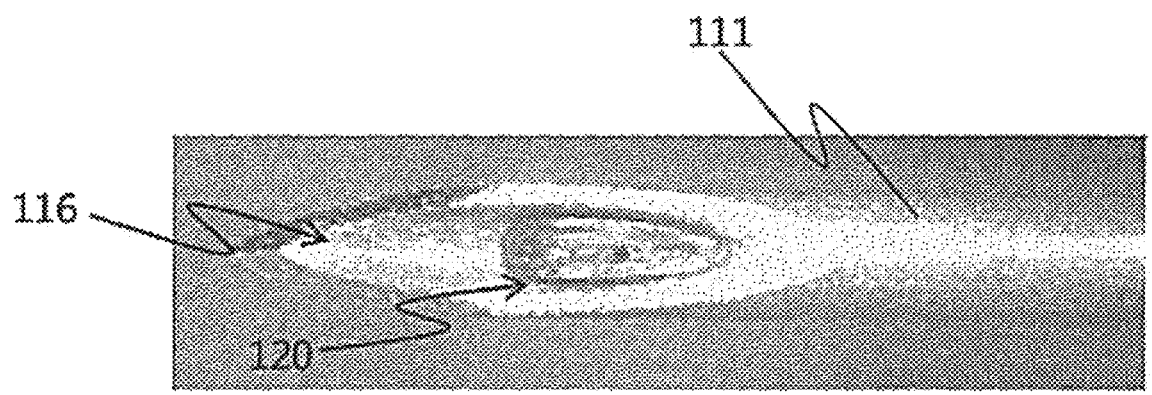
FIG. 7 is a photograph in which the laser light sensor is mounted on the injection needle of FIG. 5.

FIG. 7 shows a photograph in which the laser light sensor is mounted on the injection needle of FIG. 5.

Referring again to FIG. 4, the laser unit includes a laser engine for generating a laser and a laser scanner for detecting the wavelength, etc. of the emitting laser.

The OCT detection unit comprises an OCT scanner for detecting the wavelength, etc. of an OCT beam that is reflected by the emitted laser in the cornea, etc. and an image processing unit for visualizing a tomographic structure of two or more layers selected from the group consisting of the corneal epithelium, Bowman's membrane, corneal stroma, Descemet's membrane, and corneal endothelium.

The depth adjusting unit includes an electric motor 140 and a speed control unit.

The electric motor 14 adjusts the position of the cylinder 114 while being in contact with the outer surface of the cylinder 114 of the injector unit 110 to adjust the depth of the injection needle 111.

The electric motor 140 can adjust the depth of the injection needle 111 at a speed of 100 μm/sec to 500 μm/sec according to the operation of the user. Considering that the thickness of the cornea required to be reshaped is several hundred micrometers, when the insertion speed of the injection needle 111 is less than 100 μm/sec, the operation time may be delayed more than necessary because the speed is too slow. When the insertion speed of the injection needle 111 is over 500 μm/sec, it is difficult to stop the position of the injection needle 111 at a desired depth and the success rate of corneal shaping may decrease.

The speed control unit can adjust the insertion speed of the injection needle 111 according to the operation of the user. For example, the speed control unit may be a pressure sensing pedal that increases the insertion speed of the injection needle 111 as the applied pressure increases. The pressure sensing pedal can be configured to be operated by the operator's foot, so that both hands of the operator can be free, thereby remarkably improving the working efficiency of the operator.

The surgical apparatus 100 further includes a control unit for controlling the laser unit, the OCT detection unit, and the depth adjusting unit.

Specifically, the control unit can control the depth adjusting unit to prevent the injection needle from being inserted over the set depth, thereby preventing the injection needle from being inserted beyond the anatomical interface set by the operator inadvertently. Nonetheless, it is also possible to adjust the injection needle so as to be inserted to a depth more than manually set.

The surgical apparatus 100 further includes an alarm device controlled through the control unit, and the control unit can control the alarm device such that the alarm sounds when the injection needle reaches the set depth. By including the alarm device, it is possible to prevent the injection needle from being inserted beyond the anatomical interface set inadvertently by the operator.

In one example, the set depth may be the depth of one of the anatomical interfaces between the corneal epithelium, Bowman's membrane, corneal parenchyma, Descemet's membrane, and corneal endothelium, and the area required for the lamellar keratoplasty may be set after confirmation through an OCT-based image processing unit.

While the present invention has been described in connection with the drawings of certain exemplary embodiments, a person skilled in the art may make various modification and application within the scope of the present invention based on the foregoing description.

INDUSTRIAL APPLICABILITY

As described above, the surgical apparatus for lamellar keratoplasty according to the present invention includes a laser light sensor which is located on the inner side of the bevel structure of the injection needle and connected to the laser unit and the OCT detection unit through an optical fiber, and a depth adjusting unit for adjusting the depth of the injection needle in the cornea according to the user operation, thereby significantly improving the success rate of the lamellar keratoplasty by accurately reshaping the cornea with less variation in reproducibility.

The invention claimed is:

1. A surgical apparatus for dissecting a part of a cornea during lamellar keratoplasty, comprising:
   an injector unit including a hollow injection needle having a bevel structure at one end;
   a laser unit for emitting a laser for OCT imaging;
   an OCT detection unit for photographing a tomographic image of the cornea using the laser;

a laser light sensor located on an inner surface of the bevel structure of the injection needle, and connected to the laser unit and the OCT detection unit through an optical fiber; and a depth adjusting unit for adjusting a depth of the injection needle in the cornea according to an operation of a user.

2. The surgical apparatus of claim 1, wherein the injector unit includes:

a cylinder;

a piston having an outer diameter corresponding to an inner diameter of the cylinder;

a coupling tube communicating with the cylinder, positioned at one end of the cylinder, and having a narrowing outer diameter; and a fixing tube communicating with the coupling tube and having an inner diameter corresponding to the outer diameter of the coupling tube, the fixing tube being connected to the coupling tube in a fitting manner and fixing the injection needle on the opposite side of the coupling tube.

3. The surgical apparatus of claim 2, wherein the optical fiber connected to the laser light sensor is located in the injection needle, and the optical fiber is connected to the laser unit and the OCT detection unit by extending outward through a portion where the coupling tube and the fixing tube are connected in the fitting manner.

4. The surgical apparatus of claim 2, wherein the piston compresses air in the cylinder either manually or electrically so that the air is discharged through the injection needle when the injection needle reaches a set depth in the cornea.

5. The surgical apparatus of claim 2, further comprising an alarm device controlled by the control unit, and the control unit controls the alarm device such that the alarm sounds when the injection needle reaches the set depth.

6. The surgical apparatus of claim 1, wherein the laser light sensor has a slope structure in which one end of the laser light sensor has an angle of 30 to 60 degrees such that laser light can be injected toward an opened direction of the bevel structure of the injection needle, and a reflection portion for reflecting the laser is formed in the slope structure of the laser light sensor.

7. The surgical apparatus of claim 6, wherein the reflection portion has a structure in which a metal is coated or a mirror is attached on an outer surface of the slope structure.

8. The surgical apparatus of claim 1, wherein the laser unit includes a laser engine and a laser scanner.

9. The surgical apparatus of claim 1, wherein the OCT detection unit includes an OCT scanner and an image processing unit, and the image processing unit visualizes a tomographic structure of at least two layers selected from the group consisting of the corneal epithelium, Bowman's membrane, corneal stroma, Descemet's membrane and corneal endothelium based on an electrical signal of the OCT scanner.

10. The surgical apparatus of claim 1, wherein the depth adjusting unit includes an electric motor for adjusting a position of the cylinder while being in contact with the outer surface of the cylinder of the injector unit to adjust the depth of the injection needle.

11. The surgical apparatus of claim 10, wherein the electric motor adjusts the depth of the injection needle at a speed of 100 μm/sec to 500 μm/sec.

12. The surgical apparatus of claim 10, wherein the depth adjusting unit further includes a speed control unit for adjusting an insertion speed of the injection needle according to an operation of a user.

13. The surgical apparatus of claim 12, wherein the speed control unit is a pressure sensing pedal that increases the insertion speed of the injection needle as the applied pressure increases.

14. The surgical apparatus of claim 1, further comprising a control unit for controlling the laser unit, the OCT detection unit and the depth adjusting unit.

15. The surgical apparatus of claim 14, wherein the control unit controls the depth adjusting unit to prevent the injection needle from being inserted over the set depth.

16. The surgical apparatus of claim 15, wherein the set depth is a depth of one of the anatomical interfaces between of the corneal epithelium, the Bowman's membrane, the corneal stroma, the Descemet's membrane and the corneal endothelial.

17. The surgical apparatus of claim 4, wherein the set depth is a depth of one of the anatomical interfaces between of the corneal epithelium, the Bowman's membrane, the corneal stroma, the Descemet's membrane and the corneal endothelial.

18. The surgical apparatus of claim 5, wherein the set depth is a depth of one of the anatomical interfaces between of the corneal epithelium, the Bowman's membrane, the corneal stroma, the Descemet's membrane and the corneal endothelial.

* * * * *